US00PP13655P29

(12) United States Plant Patent
Koppe

(10) Patent No.: US PP13,655 P2
(45) Date of Patent: Mar. 11, 2003

(54) BEGONIA PLANT NAMED 'BELA'

(75) Inventor: Lubbertus H. Koppe, Ermelo (NL)

(73) Assignee: Koppe Veredeling B.V., Ermelo (NL)

( * ) Notice: Subject to any disclaimer, the term of this patent is extended or adjusted under 35 U.S.C. 154(b) by 0 days.

(21) Appl. No.: 10/077,380

(22) Filed: Feb. 15, 2002

(51) Int. Cl.[7] ..... A01H 5/00
(52) U.S. Cl. ..... Plt./349
(58) Field of Search ..... Plt./349

(56) References Cited

PUBLICATIONS

UPOV–ROM GTITM Computer Database 2002/03, GTI Jouve Retrieval Software, Citation for Begonia 'Bela'.*

* cited by examiner

*Primary Examiner*—Bruce R. Campell
*Assistant Examiner*—June Hwu
(74) *Attorney, Agent, or Firm*—C. A. Whealy

(57) ABSTRACT

A new and distinct cultivar of Begonia plant named 'Bela', characterized by its upright and mounded plant habit; double flowers that are dark pinkish red in color and held above the foliage; and excellent postproduction longevity.

1 Drawing Sheet

BOTANICAL CLASSIFICATION/CULTIVAR DESIGNATION

*Begonia×hybrida* cultivar Bela.

BACKGROUND OF THE INVENTION

The present Invention relates to a new and distinct cultivar of Begonia plant, botanically known as *Begonia×hiemalis*, commercially known as Elatior Begonia, and hereinafter referred to by the name 'Bela'.

The new Begonia was discovered by the Inventor in a controlled environment in Ermelo, The Netherlands, in October, 1999, as a naturally-occurring whole plant mutation of *Begonia×hiemalis* 'Berseba', not patented. The new Begonia was observed as a single plant in a group of flowering plants of the parent cultivar. The selection of this plant was based on its flower coloration.

Asexual reproduction of the new Begonia by cuttings taken in a controlled environment in Ermelo, The Netherlands, has shown that the unique features of this new Begonia are stable and reproduced true to type in successive generations.

SUMMARY OF THE INVENTION

The cultivar 'Bela' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Bela'. These characteristics in combination distinguish 'Bela' as a new and distinct Begonia:

1. Upright and mounded plant habit.

2. Double flowers that are dark pinkish red in color and held above the foliage.

3. Excellent postproduction longevity.

Plants of the new cultivar differ from plants of the parent, the cultivar Berseba, primarily in flower color as plants of the cultivar Berseba have dark red-colored flowers.

Plants of the new cultivar differ primarily from plants of the cultivar Bazan, disclosed in U.S. Plant Pat. No. 11,343, in flower color as plants of the cultivar Bazan have pink-colored flowers.

BRIEF DESCRIPTION OF THE PHOTOGRAPH

The accompanying colored photograph illustrates the overall appearance of the new Begonia, showing the colors as true as it is reasonably possible to obtain in colored reproductions of this type. Colors in the photograph may differ slightly from the color values cited in the detailed botanical description which accurately describe the colors of the new Begonia. The photograph comprises a side perspective view of a typical flowering plant of 'Bela'.

DETAILED BOTANICAL DESCRIPTION

In the following description, color references are made to The Royal Horticultural Society Colour Chart, 1995 Edition, except where general terms of ordinary dictionary significance are used. The aforementioned photograph and following observations and measurements describe plants grown in Ermelo, The Netherlands, under commercial practice in a glass-covered greenhouse. Average day and night temperatures were about 20° C. during the first three to four weeks then lowered to an average day and night temperature of 19° C. until flowering. Four weeks after planting rooted cuttings in 12-cm containers, one week of long nyctoperiods of 16 hours was given followed by short nyctoperiods of eight hours until flowering. Plants used for the photographs and the description were about four months old. Measurements and numerical values represent averages for typical flowering plants.

Botanical classification: *Begonia×hiemalis* cultivar Bela.
Commercial classification: Elatior Begonia.
Parentage: Naturally-occurring whole plant mutation of *Begonia×hiemalis* cultivar Berseba, not patented.
Propagation:
*Type.*—Cuttings.
*Time to develop roots.*—About 40 days at temperatures of 20 to 22° C.

*Root description.*—Fine, fibrous, well-branched and spreading. Plants of the new Begonia have not been observed to form tubers.

Plant description:

*Plant form.*—Upright and mounded plant habit, inverted triangle; freely branching with good stem and stem base strength. Flowers are double and abundant. Plants flower continuously.

*Growth habit.*—Moderate growth rate, vigorous. Suitable for 12 to 15-cm containers. Under optimal environmental and cultural conditions, usually about four months are required to produce proportional 13-cm potted plants from cuttings. Vegetative shoots are formed at basal nodes and flowering shoots are formed at upper nodes.

*Plant height.*—About 25.5 cm.

*Plant width.*—About 42 cm.

*Leaves.*—Arrangement: Simple, alternate. Young leaves, length: About 6 cm. Young leaves, width: About 6 cm. Fully expanded leaves, length: About 9 cm. Fully expanded leaves, width: About 9.5 cm. Shape: Asymmetrical, more or less reniform. Apex: Acuminate. Base: Cordate. Margin: Doubly serrate. Texture: Glabrous, smooth. Venation pattern: Palmate. Color: Young leaves, upper surface: Darker than 147A. Young leaves, lower surface: 194A. Fully expanded leaves, upper surface: Much darker than 147A. Fully expanded leaves, lower surface: 194A to 194B. Venation, upper and lower surfaces: 147C. Petiole length: About 4 cm. Petiole texture: Pubescent. Petiole color: 180B.

Flower description:

*Flowering habit.*—Double flowers with numerous tepals arranged in axillary cymes. Usually 8 to 12 flowers per cyme. Many cymes in flower simultaneously. Flowers positioned above the foliage. Flowering continuous.

*Natural flowering season.*—Plants will flower year around regardless of nyctoperiod, however plants flower earlier and more abundantly from mid-February until November in the Northern Hemisphere.

*Flowers.*—Shape: Rounded. Diameter: About 6.5 cm. Depth (height): About 2.6 cm.

*Flower buds.*—Length: About 1.5 cm. Diameter: About 1.4 cm. Color: 47D.

*Tepals.*—Arrangement: Rosette. Shape: Rounded flabellate. Apex: Rounded. Margin, outer and inner tepals: Slightly crenate. Quantity per flower: Usually about 30 per flower. Size: Outer tepals: Length: About 3.1 cm. Width: About 3.6 cm. Inner tepals: Length: About 2.7 cm. Width: About 3.6 cm. Texture: Smooth, satiny, glabrous. Color: When opening, upper and lower surfaces: 53C to 53D. Fully opened, upper surface: 53C to 53D; flower color does not fade with subsequent development. Fully opened, lower surface: Closest to 53D.

*Flower bracts.*—Arrangement: Two, opposite. Shape: Broadly cordate. Apex: Apiculate. Margin: Serrate. Texture: Glabrous. Color, both surfaces: 139D overlain with anthocyanin, close to 53A.

*Peduncles.*—Angle: Erect. Length: About 4 cm. Texture: Pubescent. Color: Close to 180C to 180D.

*Pedicels.*—Angle: Erect. Length: About 1.2 cm. Texture: Pubescent. Color: 179C.

*Reproductive organs.*—Stamens: None observed. Pistils: None observed.

*Seed.*—Seed production has not been observed as reproductive organs are not formed.

Postproduction longevity:

*Individual flowers.*—Generally about 2 to 3 weeks.

*Whole plants.*—About 6 weeks under interior conditions.

Disease/pest resistance: Resistance to pathogens and pests common to Begonia has not been observed.

It is claimed:

1. A new and distinct cultivar of Begonia plant named 'Bela', as illustrated and described.

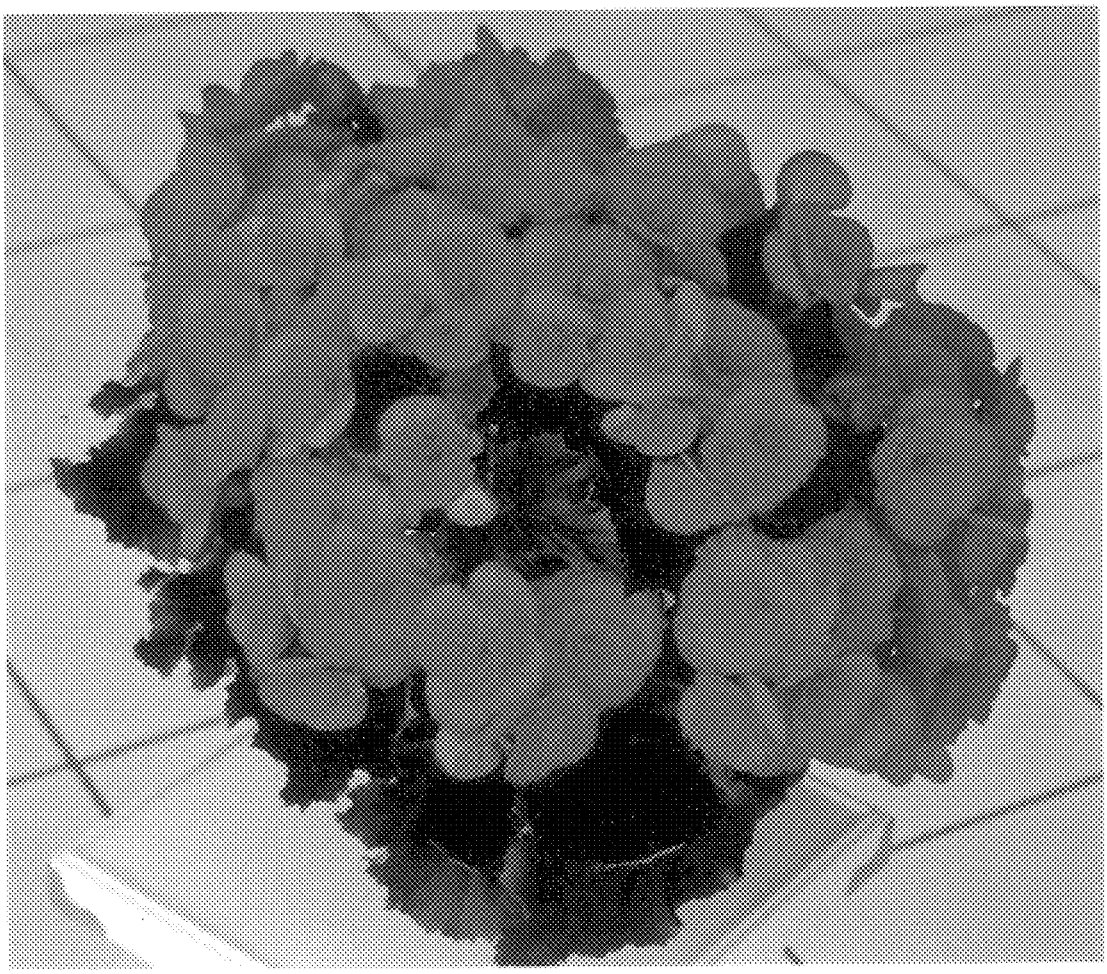

* * * * *